US007998057B2

(12) United States Patent
Kain

(10) Patent No.: US 7,998,057 B2
(45) Date of Patent: Aug. 16, 2011

(54) EROGENIC STIMULATOR WITH EXPANDABLE BULBOUS END

(76) Inventor: Melissa Mia Kain, Mulberry, FL (US)

( * ) Notice: Subject to any disclaimer, the term of this patent is extended or adjusted under 35 U.S.C. 154(b) by 843 days.

(21) Appl. No.: 12/036,502

(22) Filed: Feb. 25, 2008

(65) Prior Publication Data

US 2009/0216076 A1 Aug. 27, 2009

(51) Int. Cl.
*A61F 5/00* (2006.01)

(52) U.S. Cl. ........................................................ 600/38

(58) Field of Classification Search ............... 600/38–41
See application file for complete search history.

(56) References Cited

U.S. PATENT DOCUMENTS

| | | | | |
|---|---|---|---|---|
| 2,899,957 | A | 8/1959 | Briggs | |
| 5,127,396 | A | 7/1992 | McAllister | 600/38 |
| D384,156 | S | 9/1997 | Kain | D24/200 |
| 5,690,603 | A | 11/1997 | Kain | 600/38 |

*Primary Examiner* — John Lacyk
(74) *Attorney, Agent, or Firm* — Robert C. Kain, Jr.

(57) ABSTRACT

The stimulator includes a first resilient cylindrical (phallic-shaped) end and a second, shorter resilient cylindrical end with an expandable-deflatable bulb disposed therein. A truncated U-shaped stimulator is formed by a base connecting the ends. One embodiment permits manual bulb contraction and resilient material expansion with air or fluid ejection/admission. Another embodiment inflates the bulb manually with pressurized air/fluid (orally) with a one-way valve and user controlled valve release, or inflates the bulb with a pump. An external or on-board pump maybe used. The on-board internal pump has a depressible wall pump bladder on the stimulator. The inflatable-deflatable bulb maybe connected to the base via a reduced diameter neck. A method controllably inflates and deflates the bulb and changes its cross-sectional dimensions under user controls.

30 Claims, 5 Drawing Sheets

EROGENIC STIMULATOR WITH EXPANDABLE BULBOUS END

The present invention relates to an erogenic stimulator with an expandable bulbous end, which deflates and inflates, and optionally a suction enhancement.

BACKGROUND OF THE INVENTION

This invention pertains to sexual or erogenous stimulation devices in general and, more particularly, to a self-retained device for simultaneous use by two sexual partners such that the erotic areas of both such users are concurrently excited.

GENERAL BACKGROUND

Marital or sexual aids have been known and used throughout the centuries. Generally, such aids have been designed either for self-stimulation or for the stimulation of one party only. However, some aids satisfy two partners at the same time. This latter type of aid or stimulators is designed primarily for use by a female user and often incorporates a flexible phallic shaped stimulator secured to a base. Variations of this type of stimulator include two such phallic shapes linearly secured to opposite sides of a common or intermediate flange. Unfortunately, because of the co-linear nature of these opposite shapes, the simultaneous use of such a device by two partners requires some gymnastic-like maneuvers.

Also, it is common for these devices to not be self-retaining, that is, when one end is retained in the vagina or anal cavity, the other end is free to stimulate of the other person. Instead, these devices rely upon a series of straps in order to hold and retain the device in place on one user for proper use on the other person. However, fastening such straps prior to use is cumbersome and discomforting and causes undesirable delay.

U.S. Pat. No. 5,690,603 to Kain discloses a self-retaining stimulator, that is, when one end is retained in the vagina or anal cavity, the other end is free to stimulate the other person.

OBJECTS OF THE INVENTION

It is thus an object of the present invention to provide a marital or sexual aid that is capable of simultaneously stimulating the erotic areas of both users.

It is a further object of this invention to provide an aid that is self-retaining such that straps or other holding devices are not required, thereby eliminating any delay and discomfort.

A further object of this invention is to provide a device that is capable of being used by partners of the same sex or of the opposite sex.

Still another object of this invention is to provide a device that is capable of flexing as needed but which returns to its original position upon its release.

Yet another object of this invention is to provide an aid that is designed with no abrupt flange or base to interfere with its use or its stimulating capabilities.

An additional object is to stimulate the clitoris of one of the users with a suction element during sexual play with the stimulator.

One of the several important objects of the present invention is to employ an inflatable or expandable bulbous end, which deflates and inflates, designed to fit within an anal or vaginal cavity of one of the users or partners.

It is another object of the present invention to have a pump included in the stimulator, or be external thereof, or have a manually inflation tube-valve for the user to inflate or re-inflate the bulb.

SUMMARY OF THE INVENTION

One embodiment of the erogenic stimulator for use by two partners includes a first elongated, resilient and generally cylindrical end region (typically phallic-shaped) having a first distal end and a first proximal base end. A second resilient and generally cylindrical end region with an expandable bulbous portion, which deflates and inflates, is sized for receipt in an anal or vaginal cavity. The second end region is shorter in length than the first end region. A base is connected intermediate the first and second proximal base ends of the first and second end regions. The first and second end regions extend upwards from the base forming a truncated substantially U-shaped stimulator. A passage in the stimulator leads to the expandable bulbous end portion in the shorter second end region and permits transit of fluid or air therethrough dependent upon the action of a valve in the transit passage. One embodiment does not include a valve and the bulb manually contracts (expelling air-fluid) and thereafter expands due to the bulb's resilience. Another embodiment includes a one-way valve. The expandable bulbous portion may be manually expanded by orally injecting air into a common one way valve, may be injected with fluid with a syringe or pump, or may be inflated with air (or fluid) by an external pump or an inboard, internal pump. Alternatively, the bulbous portion may be deflated with an air/fluid valve and then re-inflated, that is, the bulbous size may be altered by expansion or contraction. The second bulbous end portion is preferably connected via a reduced diameter neck portion to the second proximal base end. A further embodiment includes an on-board pump formed by a pump bladder with a depressible pump wall on the unit. A simple version of the expandable bulbous stimulator includes a one way valve, with an operator control valve release in the valve stem, which valve leads to air passageway which leads to the inflatable bulb. A user blows up the bulb orally by compressing the valve stem and blowing pressurized air into the expandable deflatable bulb.

BRIEF DESCRIPTION OF THE DRAWINGS

Further objects of the present invention can be found in the detailed description of the preferred embodiments when taken in conjunction with the accompanying drawings in which.

DETAILED DESCRIPTION OF THE PREFERRED EMBODIMENTS

The present invention relates to a erogenic stimulator or martial aid. Similar numerals designate similar items throughout the drawings and specification.

Figure 1A:
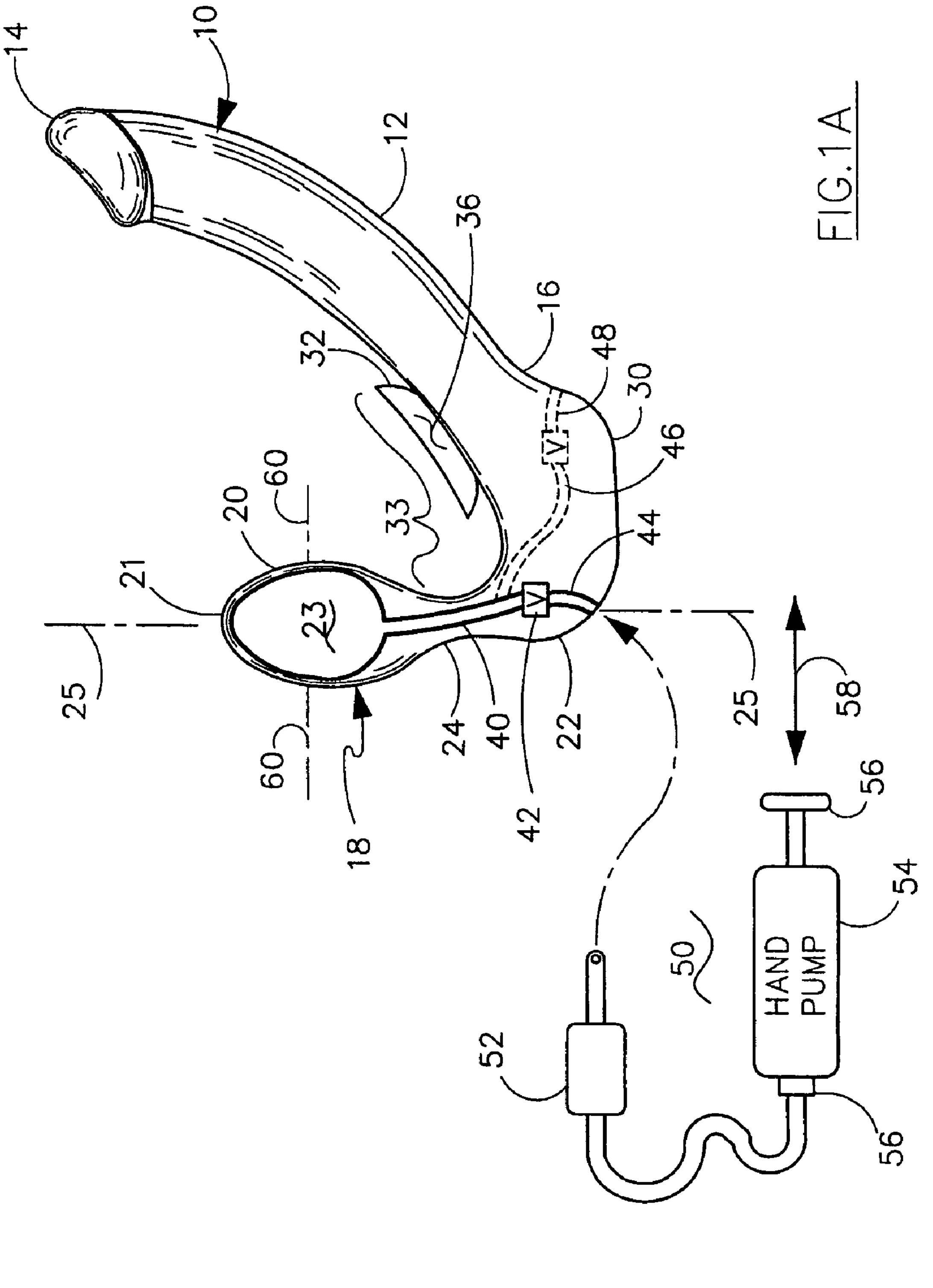
FIG. 1A diagrammatically illustrates an erogenic stimulator aid including an expandable bulbous end, which deflates and inflates, and optionally with a suction cup enhancer.
Figure 1B:
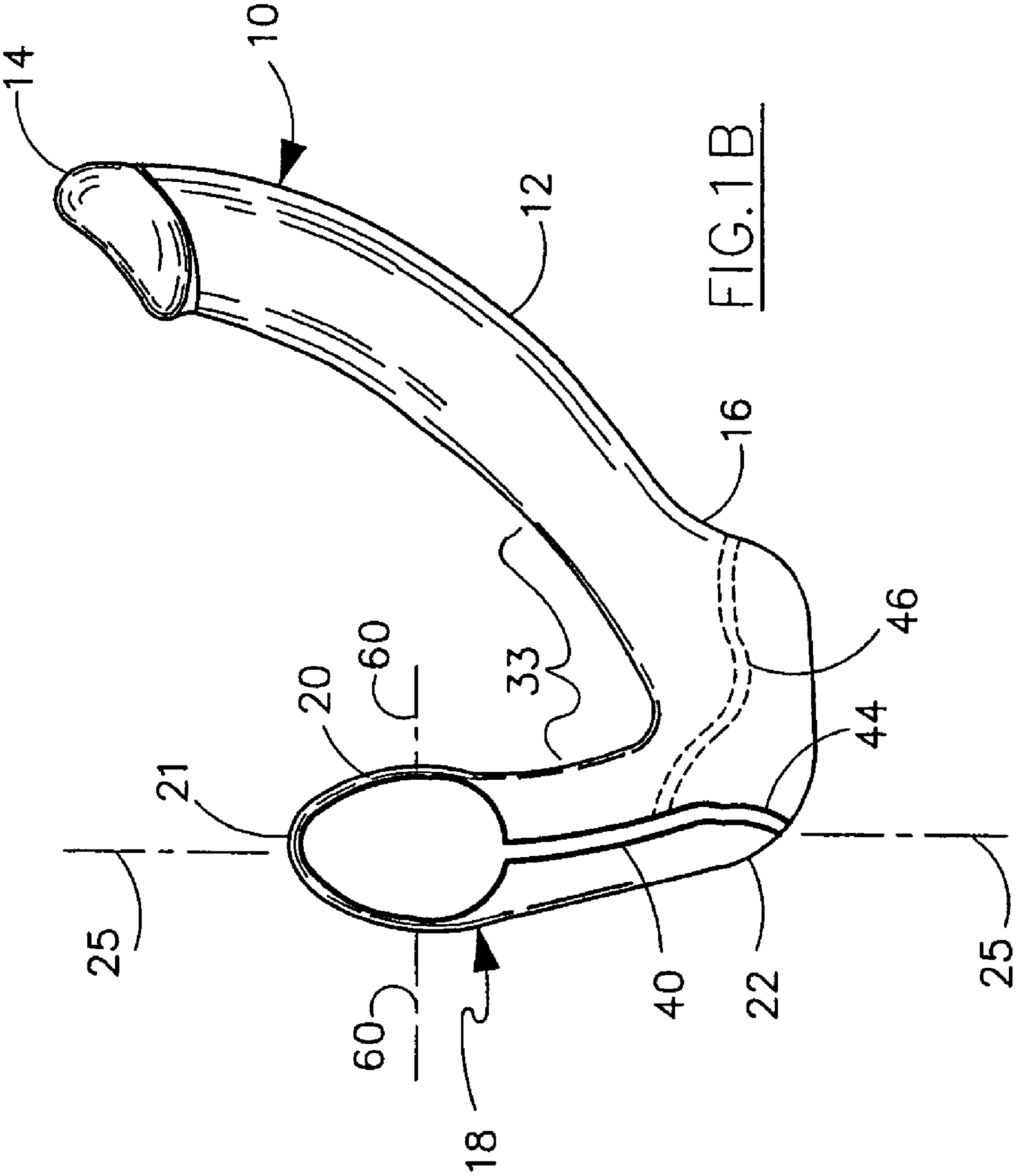
FIG. 1B diagrammatically illustrates a simple deflatable expandable bulbous end on the U-shaped stimulator.

FIG. 1A diagrammatically illustrates stimulator 10 having a first elongated, resilient and generally cylindrical end region 12. FIG. 1B is described after the pumpable or externally inflatable systems shown in FIGS. 1A, 2A, 2B and 3. In the preferred embodiment, end region 12 has a phallic shape. First end region includes a first distal end 14 and a first proximal base end generally identified at end portion 16. Stimulator 10 includes a second resilient and generally cylindrical end region 18 sized for receipt in an anal or vaginal cavity. Second end region 18 includes a second distal end 21 and an expandable bulbous end portion 20, which deflates and inflates, and a second proximal base end generally near base end portion 22. This second end region 18, and primarily expandable bulbous portion 20, is connected via a reduced diameter neck portion or neck 24 between the bulbous end 20 and the second proximal base end 22. The second end region includes distal end 21, the bulbous element 20, the neck 24 and the base proximal end 22. Neck 24 enables the user to better retain the bulbous end 20 in the body cavity. Bulbous end 20 is adapted to permit the muscle groups of one of the partners using the stimulator to hold the second end in place during use. The bulb 20 can be inflated or deflated prior to insertion or after insertion. The diameter of the neck 24 compared to the diameter of expandable bulbous portion 20 may be altered such that the neck is only slightly smaller than the expandable bulbous portion 20. The term "expandable" includes the concept of inflation and deflation. The stimulator may have some degree of flexibility such that the second end region 18 flexes with respect to the first end region 12. The degree of flexibility may be altered by (a) selection of materials; (b) the use of multiple or different materials for end regions 12, 18 or the connecting nexus structures to the base 30; or (c) employing more rigid or less rigid materials in the stimulator at key points (at non-flexible regions, see first end region 12) and resilient materials at the flex points, namely near the first and second proximal base 16 and 22. For example, the use of a rigid member in neck region 24 reduces flexibility. A reduction in the cross-sectional size of the flexing elements (see the proximal base ends) may increase flexibility. An alternative construction of the invention eliminates the reduced diameter of neck 24 such that the end region 18 has a common diameter with neck 24.

Stimulator 10 includes a base 30 connected intermediate first proximal base end 16 and second proximal base end 22. First end region 12 and second end region 18 extend upwards from base 30 and form a truncated, substantially U-shape stimulator. The U-shape is truncated since the second end region 18 is smaller in length than the first end region 12. Hence one of the legs of the U-shaped stimulator is truncated or shorter compared to the other leg. The U-shaped stimulator has a curved region 33. The U-shape of stimulator 10 may also be considered to be an L-shape due to the truncated nature of the bulbous end 18. The L-shape is rotated such that the intersection between the upper leg of the L-shape and the base of the L-shape is the location of the suction cup 32 (an optional feature herein).

A concave suction element 32 is mounted, attached or formed as part of the base in curved portion 33 of the truncated U-shape stimulator. Suction element 32 rises above or is formed on curve 33 of the U-shaped stimulator 10. Concave suction element 32 has a outer rim 34 rising above surface 35 of curve portion 33 of the truncated U-shape stimulator in the preferred embodiment. Outer rim 34 may be a circle, oval, ellipse, triangle, square, polygon, rectangle or a diamond shape. The suction element may have a low rise rim and be primarily formed by a depression in base 30. Concave suction element 32 has an interior space 36. Suction element 32 is an optional feature.

One of the important aspects of the present invention is the use of an expandable-deflatable bulbous end portion. For operation, the expandable-deflatable bulbous portion 20 must be (i) inflated with either air or fluid and (ii) the air or fluid must be entrapped therein by some type of valve. Preferably, a one way valve 42 is used which blocks fluid or air flow in transit passage 40, 44. The transit passage leads to interior bulb space 23 of expandable bulbous portion 20. The valve may be located on or near an exterior surface of the base 30 (FIG. 2B), at any interior but accessible location, or may be located near any exterior surface of the stimulator, even at distal end 14 of the first end region 10 with a transit passage 40 leading to bulbous interior space 23. Exterior or near exterior locations permit the user to activate the release control of the valve. Upon activation, the release control opens the valve and ejects air or fluid from the bulb. The material about expandable-deflatable bulbous portion 20 is flexible enough to permit expansion and contraction. In addition to inflation, some type of air/fluid release valve and passage must be included. Although it is preferable to use a one way valve which also acts as a release valve, a second valve (not shown) may be used to release the air/fluid from the expandable-deflatable bulbous portion 20. This release valve may be located at the distal end 21, or in the neck 24, or at other locations noted above. An exit passage must be provided for a second valve.

In one of the illustrated embodiments, valve 42 is a one way valve and is similar to a needle valve typically used in connection with basketballs, footballs, soccer balls and other inflatable items. Male needle valve element 52 is insertable into passage 44 and into valve 42. The distal end of the male valve stem 52 opens the one way valve 42. Pump 50 is used in this illustrated embodiment. If pump 50 is an air pump, the hand pump 54 is activated by the user moving pump handle 56 back and forth in direction 58. This action, as is known, injects pressurized air via hose coupler 56, male stem 52 and valve 42 into inflatable bulb chamber 23. The injected air inflates expandable bulbous portion 20. To release the air from expandable-deflatable bulbous portion 20, the user decouples coupler 56 while the male stem 52 is in valve 42. The presence of male stem 52 in valve 42 is a user release control for valve 42.

Rather than use an air pump, hand pump 54 may be a fluid hand pump with a fluid reservoir therein. Alternatively, a medical syringe with a fitting similar to male valve stem 52 may be employed. Other sources of pressurized air or fluid may be used with appropriate valve 42 couplers.

The invention may be used with various valves 42 as long as air or fluid under pressure is injected past valve 42 and into end bladder 23 and the valve 42 thereafter retains the fluid/air pressure therein (one way valve action). Some type of release control valve must be provided to deflate the bladder 23. By depression of base 30 near valve 42, a user may activate a control release in valve 42 and cause the release of pressurized fluid or air from end bladder 23. The ejected air/fluid from the interior space 23 is expelled into the ambient environment.

The benefits of the inflatable end bladder include inflation after insertion into the anal or vaginal cavity; deflation thereafter to provide a level of comfort for the user-wearer, or inflation-deflation before insertion into the anal or vaginal cavity to account for the different body cavity sizes or account for different muscle controls thereat. Inflation or deflation post insertion is also an option.

Figure 3:
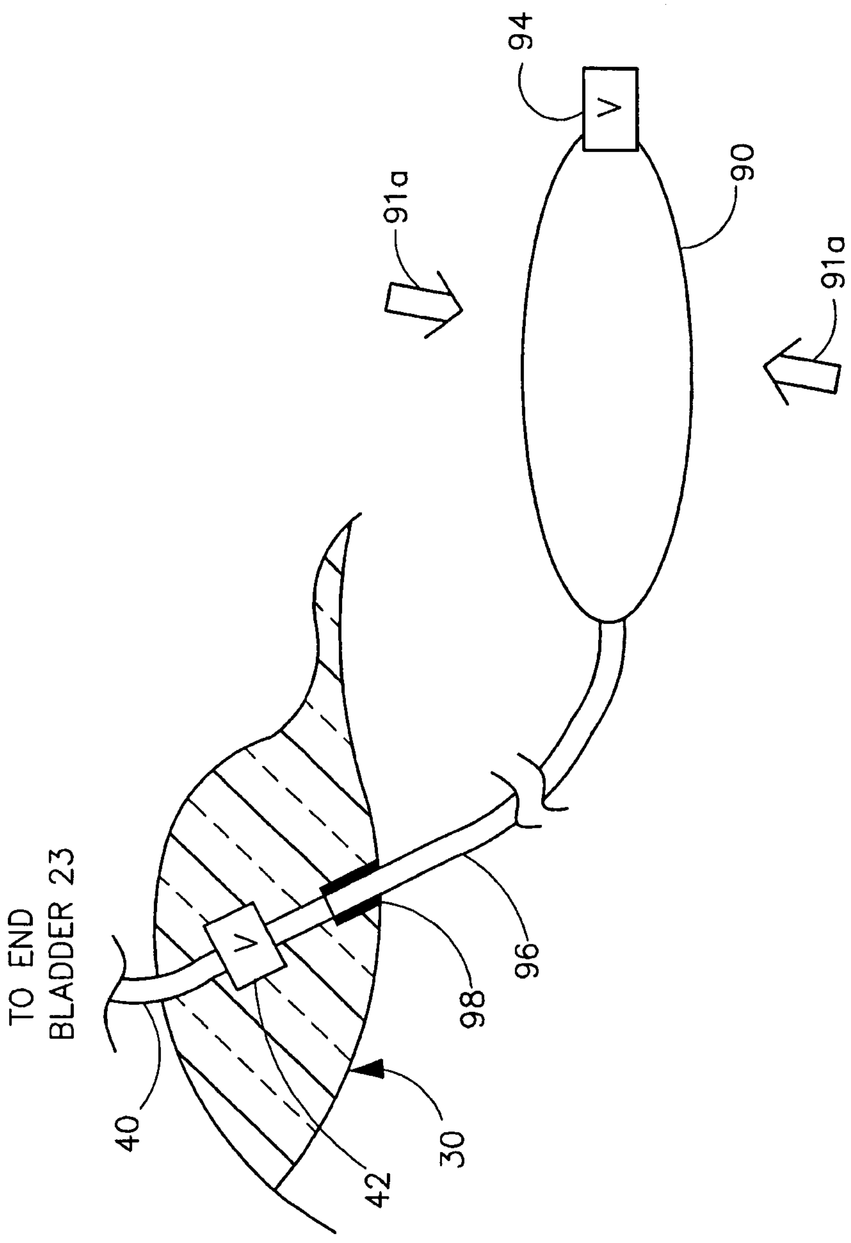
FIG. 3 diagrammatically illustrates another hand pump.

FIG. 3 illustrates that hand pump 90 may be compressed by inboard forces 91A and compressed air (or fluid, if bulb 90 is filled with fluid) is injected via coupling hose or tube 96 into base 30 of the stimulator. After passage through control valve 42, the air/fluid is delivered to the end bladder 23. In an inflation mode, control valve 42 limits outboard air/fluid flow. Control valve 42 needs a release or deflation position, not shown in FIG. 3. The tube-base coupling joint 98 should be a fairly close fit joint to facilitate the transit of air/fluid into the bulbous end bladder 23. Hand pump 900 may be configured similar to a blood pressure pump. Valve 94 permits entry of air into the bladder of pump 90.

Figure 2A:
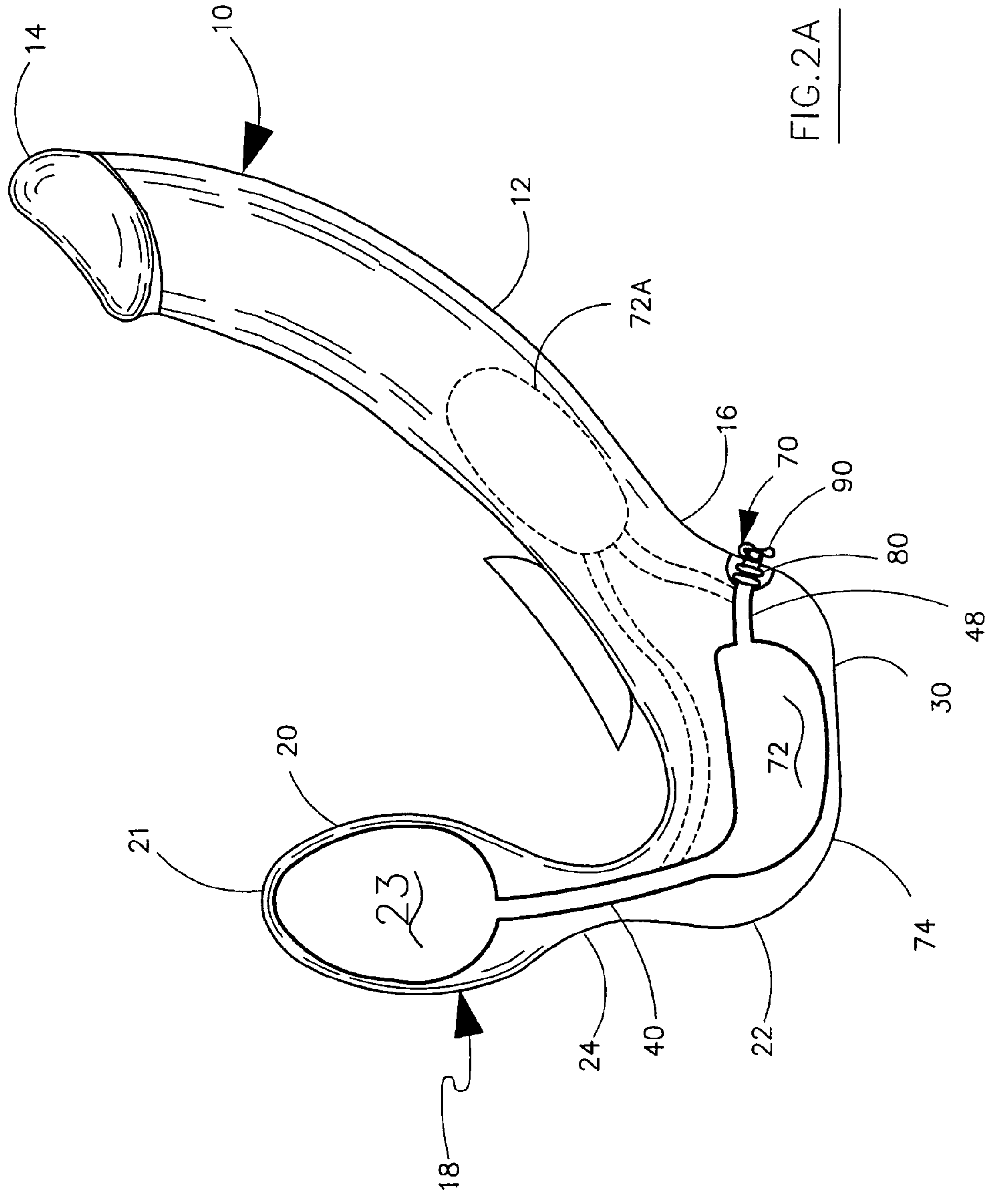
FIG. 2A diagrammatically illustrates shows (i) a one way valve enabling manual (oral) inflation (one alternate embodiment) and (ii) a base with an pump bladder (another embodiment independent or combined with the manual valve-stem inflation system)
Figure 2B:
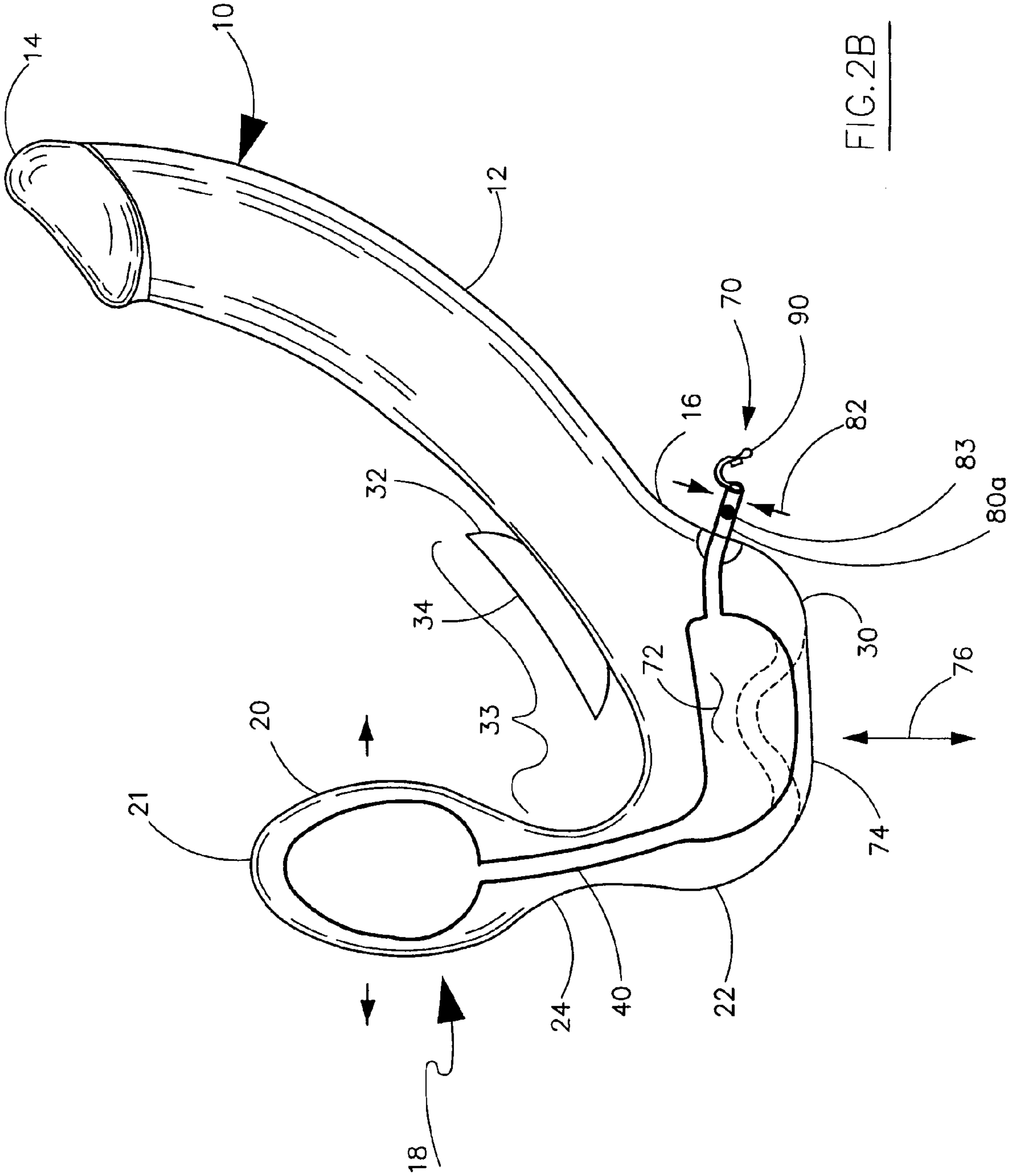
FIG. 2B diagrammatically illustrates the depressible pump bladder.

Alternately, the transit passage and valve may be placed in the base or in other parts of the stimulator as shown by the dashed lines in FIG. 2A (pump bladder 72A is in end region 12).

FIG. 2A shows both a pump included in the base 30 and, alternatively or in combination with, a manual valve 70. A simple expandable bulb stimulator would include expandable bulbous portion 20, transit passage 40 and a simple valve and valve stem 80 (and not include a built-in pump). The valve and valve stem 80 may be similar to the valve and valve stem used on beach balls and other common manually inflatable items. The common valve and valve stem 80 is extendable from base 30 (see FIG. 2B) and when cap 90 is withdrawn from the cap seat on the valve stem 80*a*, the user compresses one way air valve 83 in the direction of arrows 82, and delivers air under pressure into the passageway 40 and into the interior 23 of the expandable bulbous portion 20. One way valve 83 is closed when radially compression is withdrawn opposite arrows 82. The simple valve and valve stem 80 is therefore manually or orally operated to inflate the bladder end. Deflation is permitted when valve 83 is radially compressed per force 82. In a simple configuration, there is no need for pump bladder 72 shown in FIG. 2B. The operator release control is within valve stem 80*a* and is activated by force 82. End bladder 23 is deflated by opening valve 83 by force 82.

In a combinatory configuration, base 30 includes an embedded or onboard pump consisting of pump bladder space 72 and a depressible bladder wall 74. Wall 74 is part of the base 30. It should be noted that the pump bladder space 72 and depressible bladder wall 74 may be located at various positions in the stimulator, including the base (shown in FIG. 2B) or the first end region 12 shown in dashed lines in FIG. 2A or potentially in the neck 24. The built-in pump 72, 74 may be used with a simple one way valve and a release valve may be used to evacuate bulb bladder 20, 23. The built-in pump system may use two valves, one for inflation and a second for evacuation of chamber 20. A more complex one way valve with an operator release control may be used similar to that described above with the manual, orally activated valve. A one way valve 80 may be used (without a pull-out valve stem 80*a*) which permits only one way air flow. One way flow of fluid may be permitted if the stimulator 10 is submerged in fluid, such as water, and the built-in pump is activated. In either event, the pump 72, 74 is activated by depression of the bladder wall 74 which causes air (or fluid) to move into end bladder 23 if valve 80 is a one way valve blocking outboard air/fluid flow. For purposes of clarity, air flow is discussed herein but fluid flow is also contemplated for use with the stimulator. After depression and upon release, the resilient nature of the bladder wall 74 draws air into the bladder ("pump filling") via the valve 80 and the entrance passage 48. See FIG. 2A. If a "stiff" expandable bulbous portion 20 is needed, a secondary one way valve may be included in neck 24 or at the distal end of transit passage 40 near the bulb bladder 23. To release the air with a dual one-way valve system, compression of the secondary valve (see similar compression force 82 in FIG. 2B) is needed simultaneous with the operator release of the primary valve 80. The secondary valve keeps air in the bulb during the "pump filling" operation.

In operation, one partner places bulbous distal end 20 in an anal or vaginal cavity and the first cylindrical end region 12, preferably having a phallic shape, is inserted into an anal or vaginal cavity of the other partner. The expandable bulb is enlarged (if needed) prior to insertion into the user's body or subsequent thereto. Inflation or deflation may occur post insertion into the body cavity.

When in use, concave suction element 32 contacts the skin and erogenous zones of one of the partners. When suction element 32 (particularly rim 34) is in contact with skin or other erogenous body zone, and the stimulator 10 moves or rotates due to thrusting or rocking motion of one partner with respect to the other partner, suction is created and then released. Air is trapped when suction cavity 36 is closed. If open, air is ejected from the cavity. Thereafter upon close contact to the skin or erogenous zone, the cavity draws air therein enhancing the suction at element 32. Suction is developed by flexing action of cup 32 on the skin or erogenous zone. Therefore, the suction element 32 enhances the sexual play of the users.

The term "expandable bulbous end" also includes the concept that the bulbous end 20 can be deflated to a more comfortable size by the user. Essentially, the cross-sectional diameter of the bulbous end portion 20 is changeable, either by inflation or deflation. The cross-sectional diameter is normal or perpendicular to the longitudinal axis 25 of the bulbous end portion 20. An appropriate valve release, under the control of the user, may eject air/fluid when the bulbous end portion 20 is squeezed. Upon release of the control valve, the bulbous end is sealed and the end is smaller, at least in its cross-sectional dimension (normal to the longitudinal axis of the end region 18). Thereafter, the bulbous end portion 20 can be expanded by user controlled re-release of the valve and re-inflation of the bulbous end 20 due to the flexible return-to-shape nature of the end materials. In short, the bulb is manufactured in an inflated state. A hand valve (FIG. 2A) can release the air or fluid, or a pump draw the air or fluid out to reduce the bulb for ease of body cavity insertion. To re-inflate, the valve is opened, thereby allowing air or fluid (if the stimulator is immersed in fluid) to go back into the bulb space 23 and re-expand the bulb upon release of the valve mechanism. The bulb material, being rubber, silicone, plastic, vinyl or the like, tend to return to the "as molded" manufactured shape.

FIG. 1B diagrammatically illustrates simplified version of stimulator 10 having a first elongated, resilient and generally cylindrical end region 12, preferably a phallic shape. Stimulator 10 of FIG. 1B includes a second resilient and generally cylindrical end region 18 sized for receipt in an anal or vaginal cavity. Second end region 18 includes a second distal end 21 and an expandable bulbous end portion 20, which deflates and inflates, and a second proximal base end generally near base end portion 22. Reduced diameter neck portion or neck 24 is not shown in FIG. 1B. The second end region includes distal end 21, the bulbous element 20, and the base proximal end 22. Bulbous end 20 is adapted to permit the muscle groups of one of the partners using the stimulator to hold the second end in place during use. The bulb 20 can be inflated or deflated prior to insertion or after insertion as described herein. Bulb 20 is resilient and naturally expands to fill bulb interior space 23. The bulb 20 is deflated prior to insertion by compressive forces opposite force 60 and, in that mode of operation, the bulb inflates after insertion by its natural inclination to expand due to the elasticity of bulb 20 material, subject, of course, to the internal body cavity compressive force contrary to expansive force 60. In the second mode of operation, the bulb end 20 is inserted in its natural or resting state, and after insertion, the user's muscles about the body cavity compress the bulb 20 with compressive forces opposite force 60 and air is ejected from the bulb space 23. After removal from the body cavity, the bulb returns to the resting state size.

Base 30 is connected intermediate first proximal base end 16 and second proximal base end 22 and first end region 12 and second end region 18 extend upwards from base 30 and form a truncated, substantially U-shape stimulator or rotated L-shaped stimulator. The U-shape is truncated since the second end region 18 is smaller in length than the first end region 12. Compare the length along axial centerline 25 to the length of the first end 12. One of the legs of the U-shaped stimulator is truncated or shorter compared to the other leg. The U-shaped stimulator has a curved region 33.

The invention shown in FIG. 1B uses an expandable-deflatable bulbous end portion filled with either air or fluid. The embodiment of FIG. 1B may be modified and the air or fluid may must be entrapped in bulb space 23 by some type of valve. See FIG. 1A, valve 42 or FIGS. 2A, 2B valve system 70, 80, 80*a*, 82, 83, 90. In simple system FIG. 1B, fluid or air flows in transit passage 40 or alternate transit 46 into and out of interior bulb space 23 of expandable bulbous portion 20.

The benefits of the inflatable end bladder include natural inflation of the bulb material after insertion into the anal or vaginal cavity; deflation thereafter to provide a level of comfort for the user-wearer based upon muscle action, or inflation-deflation before insertion into the anal or vaginal cavity to account for the different body cavity sizes or account for different muscle controls thereat.

Stimulator 10 may be constructed of a rather rigid material such as hard plastic, rubber, or the like, provided that bulb end is expandable per arrows 60 in FIG. 1A. However, it is preferable for stimulator 10 to be constructed of a more compressible or resilient material, such as soft plastic or a foam material, of the type that is capable of retaining its shape and rigidity during use, but which is not so un-bending or inflexible as to be uncomfortable. Silicone is a good material to use. A thin walled bulb end 20 may be used. Also, an outer continuous covering or coating which is both smooth and slippery over such material would further enhance the enjoyment of stimulator 10. Preferably, stimulator 10 is a unitary item wherein the base, the first end region and the bulbous second end region are all made of the same flexible resilient material. Finally, it is anticipated that the angles of the legs of the truncated U-shape, that is, the general angle between the phallic end and bulbous end, would be in the range of from 60 to 80 degrees, more or less, so as to provide the most comfort during use, however, such angle may be as sharp as 45 degrees or as great as 90 degrees in some instances.

Of course, the actual length and diameter of phallic end and bulbous end can vary as needed depending on the needs of the partners. In this fashion, it is anticipated that different sizes of these ends can be offered which correspond with different sizes of the suction element and the neck portion or region so that stimulator 10 can conform to the needs and comfort levels of the intended users. The base at the curved region of the truncated U-shape may be larger or smaller than shown in relation to the phallus end and the bulbous end.

The claims appended hereto are meant to cover modifications and changes within the scope and spirit of the present invention.

What is claimed is:

1. An erogenic stimulator for use by two partners comprising:

- a first elongated, resilient and generally cylindrical end region having a first distal end and a first proximal base end;
- a second resilient and generally cylindrical end region sized for receipt in an anal or vaginal cavity, said second end region having a changeable bulbous end portion which can be inflated or deflated thereby changing a cross-sectional dimension of said bulbous end portion from a smaller dimension in a deflated state and to a larger dimension in an inflated state;
- said second end region having a second proximal base end, said second end region being shorter than said first end region;
- a base connected intermediate said first and second proximal base ends of said first and second end regions and said first and second end regions extending upwards from said base forming a truncated substantially U-shaped stimulator;
- a passage in said stimulator into said changeable bulbous end portion to permit transit of air or fluid into and out of said changeable bulbous end and expand said cross-sectional dimension or reduce said cross-sectional dimension of said changeable bulbous end portion in said inflated state and in said deflated state, respectively.

2. An erogenic stimulator as claimed in claim 1 including a valve to block said transit passage.

3. An erogenic stimulator as claimed in claim 2 wherein said valve is a one way valve permitting substantially unrestricted one-way air or fluid flow and inflation of said changeable bulbous end portion, said valve includes an air or fluid release control, operable by a user, permitting air or fluid evacuation via said transit passage only with activation of the operator release control.

4. An erogenic stimulator as claimed in claim 3 wherein said valve includes an extendible valve stem permitting inflation and deflation of said expandable bulbous end portion by a user at least orally, said user operable air or fluid release control formed in said extendible valve stem.

5. An erogenic stimulator as claimed in claim 1 wherein said transit passage includes an external port means for coupling to an external source of pressurized air or fluid.

6. An erogenic stimulator as claimed in claim 4 wherein said transit passage includes an external port means for coupling to an external source of pressurized air or fluid.

7. An erogenic stimulator for use by two partners comprising:

- a first elongated, resilient and generally cylindrical end region having a first distal end and a first proximal base end;
- a second resilient and generally cylindrical end region sized for receipt in an anal or vaginal cavity, said second end region having a changeable bulbous end portion which can be inflated or deflated and a second proximal base end, said second end region being shorter than said first end region;
- a base connected intermediate said first and second proximal base ends of said first and second end regions and said first and second end regions extending upwards from said base forming a truncated substantially U-shaped stimulator;
- a passage in said stimulator into said changeable bulbous end portion to permit transit of air or fluid into and out of said changeable bulbous end and expand a cross-sectional dimension or reduce said cross-sectional dimension of said changeable bulbous end portion;

a valve to block said transit passage; and wherein said valve is a one way valve permitting substantially unrestricted one-way air or fluid flow and inflation of said changeable bulbous end portion, said valve includes an air or fluid release control, operable by a user, permitting air or fluid evacuation via said transit passage only with activation of the operator release control.

8. An erogenic stimulator as claimed in claim 7 wherein said valve includes an extendible valve stem permitting inflation and deflation of said expandable bulbous end portion by a user at least orally.

9. An erogenic stimulator as claimed in claim 8 wherein said second bulbous end portion is connected via a reduced diameter neck portion to said second proximal base end.

10. An erogenic stimulator as claimed in claim 9 wherein said passage extends through said neck portion and into said base and said extendible valve stem extends beyond said base.

11. An erogenic stimulator as claimed in claim 7 wherein said transit passage includes an external port means for coupling to an external source of pressurized air or fluid.

12. An erogenic stimulator for use by two partners comprising:

a first elongated, resilient and generally cylindrical end region having a first distal end and a first proximal base end;

a second resilient and generally cylindrical end region sized for receipt in an anal or vaginal cavity, said second end region having an expandable bulbous end portion and a second proximal base end, said second end region being shorter than said first end region;

a base connected intermediate said first and second proximal base ends of said first and second end regions and said first and second end regions extending upwards from said base forming a truncated substantially U-shaped stimulator;

a passage in said stimulator into said expandable bulbous end portion to permit transit of fluid or air into and out of said expandable bulbous end;

a valve to block said transit passage; and a pump to deliver said fluid or air to said expandable bulbous end via said passage.

13. An erogenic stimulator as claimed in claim 12 wherein said second bulbous end portion is connected via a reduced diameter neck portion to said second proximal base end.

14. An erogenic stimulator as claimed in claim 12 wherein said valve is a one way valve.

15. An erogenic stimulator as claimed in claim 13 wherein said passage extends through said neck portion and into said base.

16. An erogenic stimulator as claimed in claim 12 wherein said pump is an air pump, said stimulator includes a pump bladder with a depressible wall operating on said pump bladder, said depressible wall located in said base or said first end region, said pump bladder pneumatically coupled via said passage to said expandable bulbous end portion and coupled to an entranceway passage leading to the ambient environment; said valve being a one way valve permitting air intake, whereby upon depression of said depressible wall, said pump bladder injects air into said expandable bulbous end portion and upon release of said depressible wall, said pump bladder draws in ambient air, said valve only permitting air intake during release of said wall.

17. An erogenic stimulator as claimed in claim 16 wherein said valve includes an air release control, operable by a user, permitting air evacuation only with activation of said operator release control.

18. An erogenic stimulator as claimed in claim 15 wherein said pump is inboard said base, said base includes a pump bladder, said base includes a depressible wall operating on said pump bladder, said pump bladder coupled via said passage to said expandable bulbous end portion and coupled to an entranceway passage in said base leading to the ambient environment; said valve being a one way valve permitting air or fluid intake but permitting air or fluid evacuation only with an operator release control, whereby upon depression of said depressible wall, said pump bladder injects air or fluid into said expandable bulbous end portion and upon release of said depressible wall, said pump bladder draws in air or fluid, said valve only permitting air or fluid intake during release of said wall.

19. An erogenic stimulator as claimed in claim 18 said valve located in said entranceway passage between said pump bladder and the ambient environment.

20. An erogenic stimulator as claimed in claim 12 including a concave suction element on said base in a curved portion of said truncated U-shape.

21. An erogenic stimulator as claimed in claim 19 including a concave suction element on said base in a curved portion of said truncated U-shape.

22. The combination of an erogenic stimulator for use by two partners and a fluid or air pump used in combination with said erogenic stimulator, the stimulator comprising:

a first elongated, resilient and generally cylindrical end region having a first distal end and a first proximal base end;

a second resilient and generally cylindrical end region sized for receipt in an anal or vaginal cavity, said second end region having an expandable bulbous distal end and a second proximal base end, said second end region being shorter than said first end region;

a base connected intermediate said first and second proximal base ends of said first and second end regions and said first and second end regions extending upwards from said base forming a truncated substantially U-shaped stimulator;

a passage in said stimulator into said expandable bulbous distal end to permit transit of fluid or air into and out of said expandable bulbous distal end;

a valve to block said transit passage; and a coupler to connect said pump to said passage for delivery of said fluid or air to said expandable bulbous distal end via said passage.

23. An erogenic stimulator as claimed in claim 22 wherein said second bulbous end portion is connected via a reduced diameter neck portion to said second proximal base end.

24. An erogenic stimulator as claimed in claim 22 wherein said valve is a one way valve, said valve includes an air or fluid release control, operable by a user, permitting air or fluid evacuation only with activation of said operator release control.

25. An erogenic stimulator as claimed in claim 23 wherein said passage extends through said neck portion and into said base.

26. An erogenic stimulator for use by two partners comprising:

a first elongated, resilient and generally cylindrical end region having a first distal end and a first proximal base end;

a second resilient and generally cylindrical end region sized for receipt in an anal or vaginal cavity, said second end region having an expandable bulbous end portion and a second proximal base end, said second end region being shorter than said first end region;

a base connected intermediate said first and second proximal base ends of said first and second end regions and said first and second end regions extending upwards from said base forming a truncated substantially U-shaped stimulator;

a passage in said stimulator into said expandable bulbous end portion to permit transit of air into and out of said expandable bulbous end;

a valve to block said transit passage; and wherein said valve is a one way valve permitting substantially unrestricted one-way air flow and inflation of said expandable bulbous end portion, said valve having an extendible valve stem, said valve includes an air release control in said valve stem, operable by a user, permitting air evacuation only with activation of said operator release control and said extendible valve stem permitting inflation of said expandable bulbous end portion by a user at least orally.

27. An erogenic stimulator as claimed in claim 26 wherein said second bulbous end portion is connected via a reduced diameter neck portion to said second proximal base end.

28. An erogenic stimulator as claimed in claim 27 wherein said passage extends through said neck portion and into said base and said extendible valve stem extends beyond said base.

29. A method of changing the size of an erogenic stimulator for use by two partners comprising:

providing a first elongated, resilient and generally cylindrical end region having a first distal end and a first proximal base end;

providing a second resilient and generally cylindrical end region sized for receipt in an anal or vaginal cavity, said second end region having a changeable bulbous end portion which can be inflated or deflated with air or fluid and providing a second proximal base end, said second end region being shorter than said first end region;

providing a base connected intermediate said first and second proximal base ends of said first and second end regions and said first and second end regions extending upwards from said base forming a truncated substantially U-shaped stimulator;

deflating said changeable bulbous end portion by compressive force thereat and blocking inboard flow of said air or fluid into said bulbous end portion by a first valve action;

inflating said changeable bulbous end portion by injecting said air or fluid therein by permitting one-way flow of said air or fluid into said changeable bulbous end portion by a second valve action; and providing a user control release for at least said first valve action.

30. The method of changing the size of an erogenic stimulator as claimed in claim 29 including changing a cross-sectional dimension of said changeable bulbous end portion by inflating and deflating.

* * * * *